United States Patent
Bowman et al.

(10) Patent No.: US 10,379,097 B2
(45) Date of Patent: Aug. 13, 2019

(54) TECHNIQUES FOR VISUALIZING HISTORICAL PATHOGEN SAMPLING IN A FACILITY

(71) Applicant: EMAP Holding LLC, Chicago, IL (US)

(72) Inventors: Larry Charles Bowman, Blacksburg, VA (US); Zygmunt John Palasz, Virginia Beach, VA (US)

(73) Assignee: EMAP HOLDING LLC, Chicago, IL (US)

( * ) Notice: Subject to any disclaimer, the term of this patent is extended or adjusted under 35 U.S.C. 154(b) by 379 days.

(21) Appl. No.: 15/147,303

(22) Filed: May 5, 2016

(65) Prior Publication Data

US 2017/0322701 A1    Nov. 9, 2017

(51) Int. Cl.
*G01N 33/15* (2006.01)
*G01N 33/02* (2006.01)
*G01N 35/00* (2006.01)
*G06T 11/00* (2006.01)
*G09G 5/00* (2006.01)

(52) U.S. Cl.
CPC .............. *G01N 33/15* (2013.01); *G01N 33/02* (2013.01); *G01N 35/00722* (2013.01); *G06T 11/001* (2013.01); *G01N 2035/0091* (2013.01); *G06T 2207/10016* (2013.01); *G06T 2207/30108* (2013.01); *G09G 5/00* (2013.01); *G09G 2340/14* (2013.01)

(58) Field of Classification Search
CPC ...................................................... G01N 33/15
See application file for complete search history.

(56) References Cited

U.S. PATENT DOCUMENTS

| | | | |
|---|---|---|---|
| 7,852,780 B1 * | 12/2010 | Eslambolchi | H04L 41/0645 370/250 |
| 2008/0300487 A1 * | 12/2008 | Govari | A61B 5/061 600/443 |
| 2009/0216438 A1 * | 8/2009 | Shafer | G01C 21/20 701/414 |
| 2010/0250561 A1 * | 9/2010 | Nishiyama | G06F 3/04817 707/754 |
| 2011/0060626 A1 * | 3/2011 | Gattino | G06Q 10/06 705/7.37 |
| 2016/0306934 A1 * | 10/2016 | Sperry | G06F 3/147 |

* cited by examiner

*Primary Examiner* — Jennifer N To
*Assistant Examiner* — Ashley M Fortino
(74) *Attorney, Agent, or Firm* — McAndrews, Held & Malloy, Ltd.

(57) ABSTRACT

A method for visualizing historical pathogen sampling in a facility includes the following steps: (1) populating a plurality of sampling locations as a plurality of icons on a map of the facility; (2) receiving sampling data specifying a plurality of pathogen levels at the plurality of sampling locations; (3) assigning one of a plurality of colors to each of the plurality of sampling locations according to the plurality of pathogen levels; (4) coloring the pathogen sampling locations on the map with the assigned colors to form a frame; (5) repeating steps (2), (3), and (4) on at least three different occasions to form a sequence of frames; and (6) sequentially displaying the sequence of frames and an identification of the respective occasion at a constant rate.

18 Claims, 3 Drawing Sheets

TECHNIQUES FOR VISUALIZING HISTORICAL PATHOGEN SAMPLING IN A FACILITY

CROSS REFERENCE TO RELATED APPLICATIONS

[Not Applicable]

BACKGROUND

This application relates to visualizing historical pathogen sampling in a facility, such as a food processing facility.

Pathogens (e.g., unwanted microbes, such as *salmonella*, *E. coli*, or *Listeria*) are a major cause of food spoilage. The presence of such pathogenic microorganisms on food products can potentially lead to food-borne outbreaks of disease and cause significant economic loss to food processors.

Pathogenic contamination of food products can occur not only from the product itself, but also from the environment. For example, food products are susceptible to contamination during processing steps carried out after the initial sanitization process. Contamination sources from the food processing environment can include processing equipment, such as knives and mixers, food contact surfaces, such as cutting boards, conveyor belts, and interior surfaces, such as floors, walls, and ceilings.

In order to evaluate the presence of pathogens, sampling can be conducted. The results of the sampling can change over time—e.g., from day to day.

SUMMARY

According to certain inventive techniques, a method implemented with a computing device for visualizing historical pathogen sampling in a facility comprises: (1) populating, with the computing device, a plurality of sampling locations as a plurality of icons on a map of the facility; (2) automatically receiving, at the computing device from a remote database, sampling data specifying a plurality of pathogen levels at the plurality of sampling locations; (3) automatically assigning, with the computing device, one of a plurality of colors to each of the plurality of icons according to the plurality of pathogen levels; (4) automatically causing coloring, as displayed on a display connected to the computing device, the pathogen sampling locations on the map with the assigned colors to form a frame; (5) automatically repeating, with the computing device, steps (2), (3), and (4) on at least three different occasions to form a sequence of frames; and (6) automatically causing sequentially displaying, as displayed on the display connected to the computing device, the sequence of frames and an identification of the respective occasion at a constant rate. The steps that are performed automatically are performed without human intervention.

The sequence of frames may be filtered according to a time range, such that only frames corresponding to within a period of the time range are sequentially displayed. Populating may be performed by dragging-and-dropping the plurality of icons, individually. The color red may be assigned to a given icon when the respective pathogen level exceeds a pre-determined threshold. The step of sequentially displaying the frames may be repeated automatically (without requiring human input) to form a loop.

The method may include one or more additional steps such as: zooming into or out from the map prior to said sequentially displaying the frames, whereby the display of frames is performed at a corresponding zoom level; fast-forwarding or rewinding during said sequentially displaying the frames; associating at least one document with an icon; or displaying the at least one document by hovering over the given icon.

The method may include the following additional steps: filtering the plurality of icons according to at least one filtering criterion to form a subset of the plurality of icons; and not displaying icons excluded from the subset of the plurality of icons during said sequentially displaying the frames.

The method may be implemented by at least one processor executing instructions stored on one or more computer-readable devices.

Figure 1:
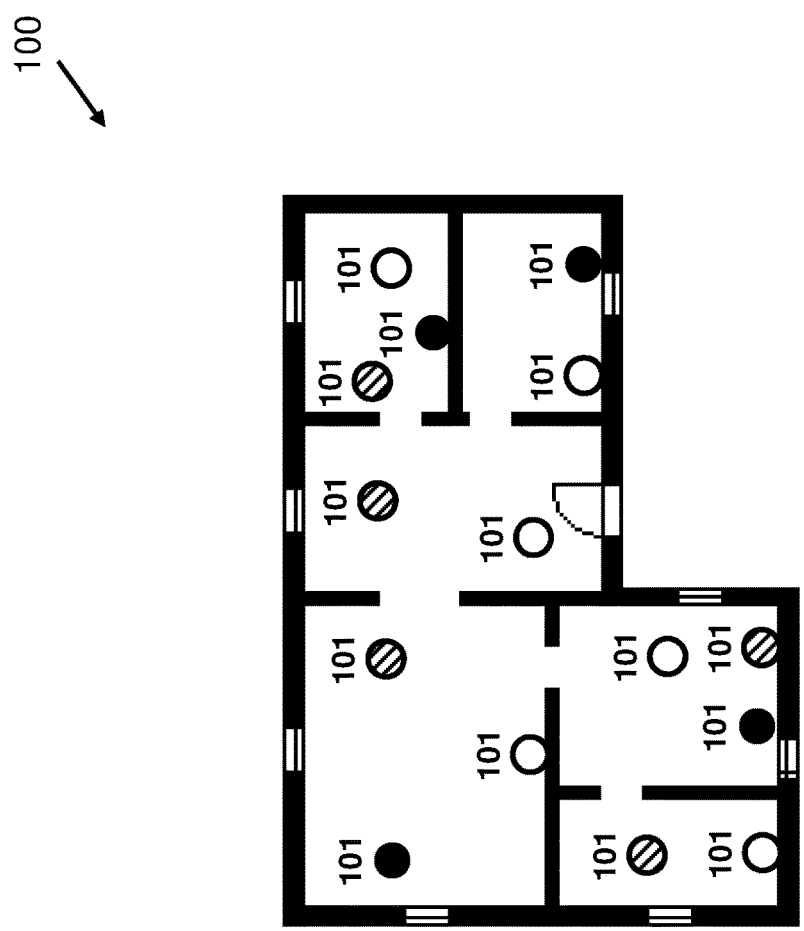
FIG. 1 illustrates a facility map with a plurality of sampling locations having different "colors" (which are depicted as having different type of shading).

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION

Inventive techniques disclosed herein allow for visualization for pathogen sampling in a facility (or a portion thereof) in a time-lapse view. Type of facilities may include food manufacturing plants, laboratories and pharmaceutical manufacturing plants Certain inventive techniques include assembling a log of collections at a plurality of sampling locations over time, associating documents to a collection, capturing and viewing images of sampled locations on a facility map, associating images to sampled locations, and/or providing a time-lapse view of the collections and associated documents and images on the facility map.

The inventive techniques may be designed for use in work and storage areas where biological samples are collected to test for compliance with environmental standards and regulations. The physical layout of these areas or a facility are shown in maps. Collections are scheduled on a calendar, and may involve samples at multiple sampling locations over multiple dates. Such a schedule may be repeated in a regular pattern. Specific sampling locations, where samples are collected, may be represented by circular icons that may be placed on a map to represent the location where samples are to be taken. For purposes of representation on a map, movable sampling locations, such as carts and tables, may be represented at a location where they are normally stored or situated. More precise identification of where samples are collected at a location may be provided in a description referencing details of objects located at the sampling location and by annotations on images of the sampling location and its objects. Sampling locations may be grouped together by drawing a closed area on a map so as to include the sampling locations within the group. Documents can be associated with collections, images can be associated with sampling locations, and the particular location of a sample can be identified on a map and on an image.

FIG. 1 illustrates a facility map 100 with a plurality of sampling location icons 101 having different "colors" (which are depicted as having different type of shading). It is also possible that shading, icon shapes, and/or the like can be used to distinguish sampling location icons 101. Sampling location icons 101 are positioned at locations in the facility at which physical samples are taken. The map 100 may be populated by dragging and dropping icons 101 onto a desired location. The icons 101 may be individually or collectively dragged, for example, from a sidebar. Populating may also be achieved through other techniques, such as right-clicking, drop-down menus, or the like. The sampling location icons 101 may be moved around on the map 100, for example, though dragging and dropping actions.

Two or more of the sampling location icons 101 may be grouped together. A user may define an area on the map 100, and sampling location icons 101 that fall within the area are grouped. By drawing groups, users are able to add or move sampling location icons 101 to any position on the map and have that site automatically associated with a given group. Grouping of sampling locations may allow data to be summarized by a specific characteristic such as the room, machine or type. Drawing these groupings on the map and then having new sampling location automatically assigned these characteristics may result in more accurate data with less user input.

Icons 101 are colorized based on the result of a pathogen sampling test. If a given pathogen's level is below an acceptable threshold, then an icon 101 may be colored green. If the pathogen level is above the threshold, the icon 101 may be colored red. If the level is approaching an unacceptable amount, then the icon 101 may be colored yellow. Other coloring schemes are possible, such as having darker shades of colors corresponding to a greater number of unacceptable results and lighter shades appearing for locations with fewer unacceptable results. Color schemes may be defined by the user, with any color being an option for any combination of criteria, such as having all suspect results in room A appear purple and all suspect results in room B appear orange. For the purposes of this application, colors are represented as follows: no shading=green; cross-hatch shading=yellow; black shading=red.

Figure 2:
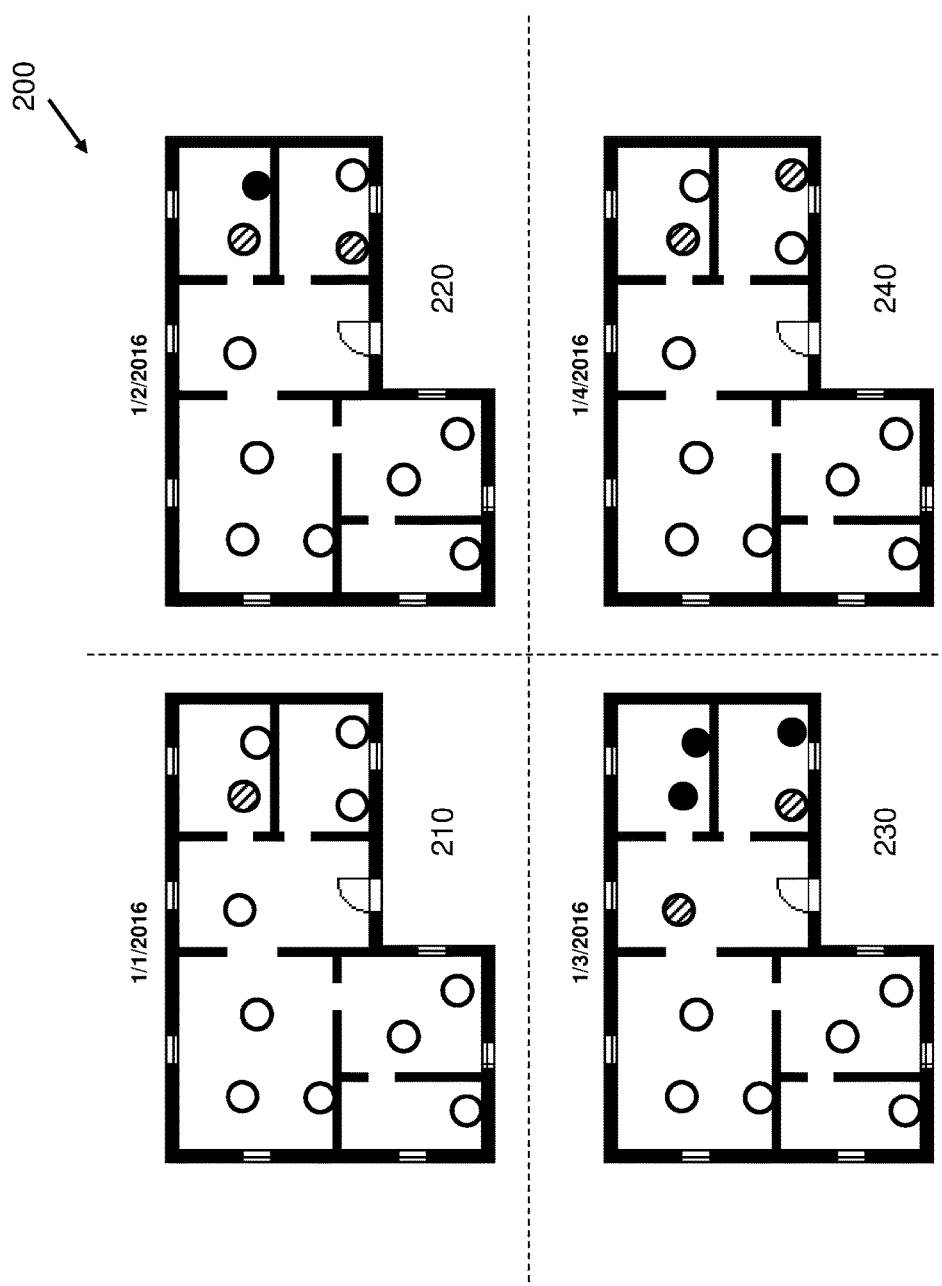
FIG. 2 illustrates a sequence of facility maps over time showing that the colors of sampling locations change over time.

FIG. 2 illustrates a sequence 200 of facility maps over time. The maps may be displayed along with an identification of the occasion corresponding to the date or time of the map. As shown in the example in FIG. 2, map 210 displays data corresponding to Jan. 1, 2016 (e.g., the date the samples were taken). Map 220 displays data corresponding to Jan. 2, 2016. Map 230 displays data corresponding to Jan. 3, 2016. Map 240 displays data corresponding to Jan. 4, 2016. The maps show how colors of icons 101 can change over time. Maps with colorized icons may also be referred to as frames. The frames may be displayed in a sequence (e.g., one at a time).

Figure 3:
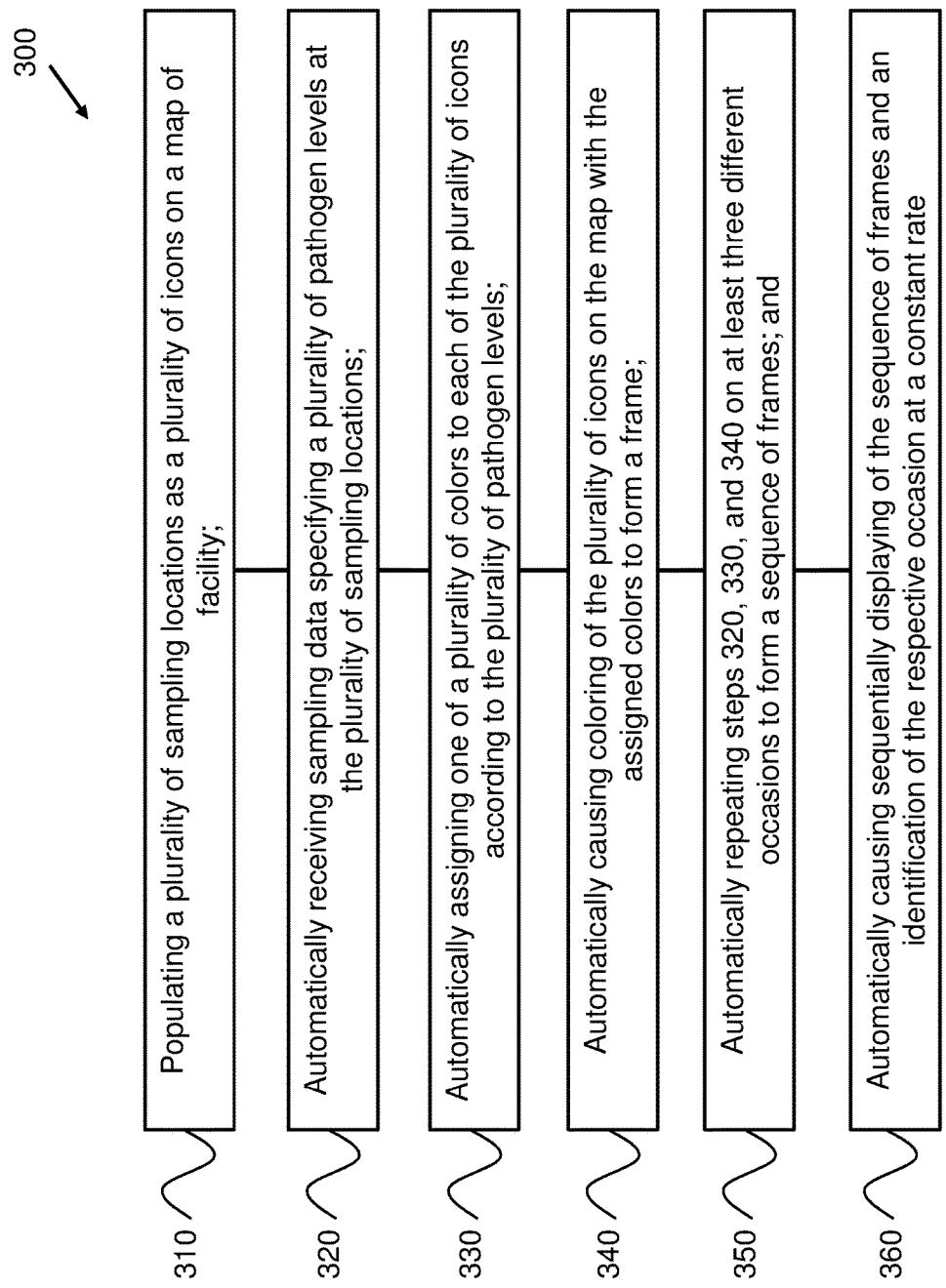
FIG. 3 illustrates a flowchart for a method of visualizing historical pathogen sampling.

A method for visualizing historic pathogen sampling in a facility is illustrated in flow chart 300 depicted in FIG. 3. The frames shown in FIG. 2 may be used in conjunction with the principles disclosed in the flowchart and described below.

At step 310, a plurality of sampling locations may be populated and represented as a plurality of icons on a map of the facility. Population may be performed with a computing device and as discussed above with respect to FIG. 1—e.g., dragging-and-dropping, right-clicking, drop-down menus, etc. As used herein, actions that are performed automatically are performed without human intervention. According to one technique, icons may be dragged-and-dropped from a sidebar onto the facility map.

An icon may be moved to a new location by, for example, selecting the icon and moving it with arrows or a mousing device. Another option is to drag-and-drop the icon to a new location.

At step 320, sampling data specifying a plurality of pathogen levels at the plurality of sampling locations is automatically received. For example, sampling data may be received at the same computing device that was used to perform population in step 310. Samples may be taken at the sampling locations. The samples may then be sent to a laboratory for testing, which may generate sampling data. The laboratory may then send the sampling data (e.g., pathogen levels) to the computing device. Alternatively, the sampling data may be retrieved by the computing device, either automatically or by prompting from a user.

According to one technique, the computing device and associated printer(s) may be implemented to generate a list and/or corresponding identifying labels (e.g., bar-code labels, RFID labels, etc.). The list and/or labels may correspond to and identify the various sampling locations. A user may then go to the sampling locations and take samples (e.g., with a swab) and store the samples in a container (e.g., a vial). The container may be labeled with a characteristic that can ultimately be used to identify the location at which the sample was taken. The container may be labeled, for example, with the appropriate identifying label generated by the computing device and corresponding printer(s).

Sampling may be performed on different occasions, aperiodically or periodically (e.g., once per day). Sampling data, then, may be generated by the laboratory and made available on aperiodic or periodic intervals subsequent to sampling.

At step 330, a color is automatically assigned, by the computing device, to each of the icons according to the pathogen levels. For example, if a pathogen level is below a first threshold, a color such as green may be assigned. If a pathogen level is above a second threshold, a color such as red may be assigned. If a pathogen level is between the first and second thresholds, a color such as yellow may be assigned. At step 340, the plurality of icons is caused to be colored, on a display connected to the computing device, with the assigned colors. The resulting map with the colored sampling location icons (either before or after it is displayed on the display) may be termed a frame.

At step 350, steps 320, 330, and 340 are automatically repeated on at least three different occasions to form a sequence of frames. For example, steps 320, 330, and 340 may be repeated on three consecutive days. Of course, it may be possible to repeat steps 320, 330, and 340 more than three times, such as four, 10, or 100 times.

At step 360, the sequence of frames is automatically caused to be sequentially displayed, by the computing device on the display connected to the computing device, along with an identification of the respective occasion. The sequence of frames may be displayed at a constant rate—e.g., the rate of display for each of the frames may be constant. Examples of such a rate are 300 ms/frame, 800 ms/frame, or 3000 ms/frame. The rate of display may be automatically or manually adjustable. This step may be performed automatically—i.e., without human intervention. It may be possible to manually initiate display of the sequence of frames, but still have the sequence automatically displayed once it has been initiated. For example, a user may interact with the computing device in an appropriate manner to start the sequence of frames rolling, and then the computing device causes the frames to be displayed in a sequence in an automatic manner.

It may be possible to filter the sequence of frames, for example, according to a time range, such that only frames corresponding to within a period of the time range are sequentially displayed. It may also be possible for a user to zoom in or out of the map (using zoom in/out icons or other shortcut keys), either before the sequence of frames is displayed or while the sequence of frames is displayed. In this case, the display of frames may be performed at a corresponding zoom level.

It may be possible to automatically repeat the sequence of frames as a loop—i.e., the first frame is automatically displayed after the last frame. This looping step may use the same constant rate as step 360. It may also be possible to fast-forward or rewind during sequential display. In such a case, the rate of display may momentarily change while the fast-forward or rewind activity is taking place (e.g., the rate goes up). It may also be possible to pause the sequence, and then resume.

It may also be possible to filter the plurality of icons according to at least one filtering criterion to form a subset of the plurality of icons. Icons excluded from the subset may not be displayed during the sequential display (or before). Such criteria may include room identification, sampling type, identification of sample collector, or risk level.

It may be possible to allow a user to specify the exact location that a sample was taken. As part of entering the sample's information, a user can click on the map to define where the sample was taken. This information is then stored with the specific sample and can be reviewed later. For example, a user may click on the capture site location icon (next to the sample the user wishes to record the sampled location for) and a map is displayed. The user may then zoom in or pan around to find the exact location of the sample. When ready, the user may click on the map at the location the sample was taken and a sampling location icon is drawn on the map at the location the user.

It may also be possible to capture a sample's location on an image. A user may specify the exact location that a sample was taken. As part of entering the sample's information, a user can draw or highlight on an associated image to define where the sample was taken (e.g., the specific area of a cart or a conveyor belt or another piece of equipment where the sample was taken from). This information may then stored with the specific sample and can be reviewed later. According to this technique, a user may click on the capture site on image icon (next to the sample the user wants to capture this information for) and an image may be displayed. The user can the zoom in or pan around to find the exact location that the given sample was taken. When ready, the user will draw or highlight on the image to display the samples exact location. The user then clicks "save changes" and this information is stored with the sample.

At a macro level, a collection audit log may track all or many of the actions that are performed that relate to a given collection set (e.g., the collection of samples on a given day). As each action happens, the audit log may be updated to account for what just occurred, who performed the action and what date and time it happened. The audit log may then available for reviewing what has occurred with an individual collection. According to this technique, users may able to perform various actions on a collection (these are user defined actions, but can include submitting, sampling, editing, or re-sampling). Upon completing such an action, the audit log is automatically updated. At a later point, a user can review the audit log and view what has occurred with the given collection by going to the review audit log context menu option.

The method illustrated by flowchart 300 may be performed in the following manner and in the following contextual activity. First, at step 310, a user drags and drops a plurality of icons onto a map of the facility using a computing device. Each icon represents a sampling location.

Then, a user prints out a list of the sampling locations along with other data—e.g., associated images with the sampling locations, associated documents (e.g., human-readable instructions to a human sample collector) associated with the sampling locations, or the like. Using the printout, the user may physically go to the sampling locations in the facility and collect biological samples in vials. Each vial may be identified to have a particular sampling location—e.g., with a barcode. The vials may then be sent to a laboratory. The laboratory may then test the samples for pathogens (e.g., *salmonella* or *E. coli*). The laboratory may provide a pathogen level for each sampling location, or for a subset thereof. For example, some locations may be tested for *salmonella* and others may be tested for *E. coli*. Some locations may be tested for both *salmonella* and *E. coli*. The resulting pathogen levels in association with the sampling locations and the occasion on which the samples were collected may form sampling data.

Next, at step 320, the resulting sampling data may be received by the computing device—e.g., automatically or manually. For example, the sampling data may be stored in a database remote from the computing device. The computing device may be alerted via a network between the database and the computing device (i.e., a secure connection via the internet) when new sampling data is available. The computing device may then retrieve the sampling data which is identified by the occasion (e.g., date and/or time) at which the samples were collected. Other examples may include having the database automatically send data to the system over a secure connection or having the system poll a specific remote directory, at some interval, and processing any data that is found.

At step 330, a red color is assigned to a sampling location icon when a pathogen level is high. A yellow color is assigned to a sampling location icon when the pathogen level is moderate. A green color is assigned to the sampling location icon when the pathogen level is low. High, moderate, and low levels may be set by two thresholds (yellow/red threshold and yellow/green threshold). While the assignment happens automatically, the criteria for this assignment may be determined by the user. At step 340, the computing device causes a connected display to display the colored icons on the map. This forms a frame.

The first collection takes place on day one. Subsequent collections and performance of steps 320-340 take place on days two through ten—one collection and performance of steps 320-340 per each day. Except for the manual collection, the process takes place automatically—i.e., steps 320, 330, and 340 are automatically repeated.

On day ten, a user wants to view the sequence of frames from days one through ten. The user clicks on an icon to initiate display of the sequence of frames (one per day). At step 350, the computing device automatically causes sequential display of the ten frames (one, two, three, . . . ten) at a constant rate (e.g., two seconds per frame). After the tenth frame, the first frame is displayed again and the sequence automatically starts over and plays in a loop until interrupted by the user.

The user then pauses the sequential display by interacting with a pause icon. The user then resumes display by again interacting with the play icon. The user fast-forwards to more quickly go through the frames. The user then rewinds to go through the frames in reverse order—either at a more rapid rate or at the original constant rate. The user then zooms in and only a portion of the map is displayed in the frame-by-frame sequence. The user zooms back out. The user then interacts with the computing device to set the start and finish date of the sequence to the third and seventh days. The user then resumes display of the sequence of frames, but this time, only the third through seventh frames are displayed in a loop.

The user then stops display of the sequence and decides that only the *salmonella* testing locations should be displayed. The user interacts with the computing device to set this filtering criterion. Based on this filtering criterion, only the *salmonella* testing locations are displayed, and the other pathogen-type sampling locations are hidden. The aforementioned processes then repeat themselves as described, but the excluded sampling location icons are hidden.

It may also be possible to associate a document (e.g., a text document or an image) with an icon. It may be possible to drag-and-drop an icon of the document onto the sampling location icon. It may also be possible to interact with the sampling location icon (e.g., right click) and then browse for a document to associate with the sampling location icon. Associated document(s) (e.g., image(s)) may be displayed in a pop-up window by hovering over a given sampling location icon with a cursor. It may also be possible to open an associated document through other means—e.g., right-clicking on the sampling location icon and selecting from a pop-up menu the desired associated document.

The capability of a time-lapse view begins with an audit log of sampling collections. The collection audit log tracks all actions that are performed that relate to a given collection. The actions for a given collection are described in a document used by the person taking the samples. For example, such a document may be a printout showing the map (or maps) covering the sampling locations for the collection, each of which may be numbered. Below the map may be a numbered row—i.e., the numbers corresponding to the sampling locations on the map. In the row may be a description of the sampling to be done and, if appropriate, a thumbnail of an image of the site. As each action happens, the audit log may be updated to account for what just occurred, who performed the action, and/or what date and time it happened. The audit log may then be available for reviewing what has occurred with a given collection. Reference documents may be associated with a collection, typically by dragging and dropping a document to the desired collection in the calendar. Similarly, images (such as photographs taken of sites covered by a collection) may be associated with a sampling location in the computer records of the system, for example, by dragging and dropping an image file onto the appropriate sampling location icon on a map. In addition, the image itself may be annotated to show where the sample was taken. Also, the location where a sample was taken can be identified on a map, causing a sampling location icon to be placed there.

In the time-lapse view the results may be displayed for the user as a series of map images that play sequentially. The user may structure the time-lapse to focus on a particular collection or a particular group of sampling locations, and may be able to use a zoom control to expand or contract the map so that the map image encompasses the sites of interest. The user may specify a date range, and maps that represent site's samples and results within that range will may play in a loop with each map image corresponding to a specific date within the user provided range. When the user starts the time-lapse view, a map that corresponds to the first date in the range may be displayed, along with those sampling locations of interest that were sampled on that date. The number of samples taken may be shown on the site icon. After a time period, the date may automatically advance and display a map that corresponds to the next date. This pattern may continue in a repeating loop through the date range until the user interacts with the computer to cause the loop to stop. As an option, the user may drag a slider to a specific date, rather than waiting for it to play.

The time-lapse sequence of map images may show the same map from frame-to-frame, thereby highlighting any changes, for example, changes at a sampling location or locations as indicated by color coded icons showing the status of each site and other parameters of interest to the user. The user may filter the display to look at one sampling location at a time or jump between sampling locations or, where a collection involves more than one map, one map at a time, over the time-lapse sequence. A map image thus identified by its changes can then be examined in greater detail.

The techniques described herein may be beneficial by providing an easily accessible way of reviewing and understanding sampling routines and results on a day-to-day basis. The level of detail being captured may make it easier in a time-lapse view to pinpoint contaminated areas and therefore provide faster response times when containing an outbreak.

Aspects of the techniques described herein (e.g., the method described in association with FIG. 3) may be implemented in digital electronic circuitry, computer software, firmware, or hardware, including the structures disclosed herein and their structural equivalents, or in various combinations. Aspects of the techniques described herein may be implemented as one or more computer programs, for example, one or more sets of program instructions residing on or encoded in a computer-readable storage medium for execution by, or to control the operation of, one or more processing units. Alternatively or in addition, the instructions may be encoded on an artificially-generated propagated signal, for example, a machine-generated electrical, optical, or electromagnetic signal that may be generated to encode information for transmission to a suitable receiver apparatus for execution by one or more processing units. A computer-readable medium may be, or be included in, a computer-readable storage device, a computer-readable storage substrate, a random or serial access memory array or device, various combinations thereof. Moreover, while a computer-readable medium may or may not be a propagated signal, a computer-readable medium may be a source or destination of program instructions encoded in an artificially-generated propagated signal. The computer-readable medium may also be, or be included in, one or more separate physical components or media (for example, CDs, disks, or other storage devices).

Certain techniques described in this specification may be implemented as operations performed by one or more computing devices on data stored on one or more computer-readable mediums or received from other sources. The term "computing device" may encompass various kinds of apparatuses, devices, or machines for processing data, including by way of example a central processing unit, a microprocessor, a microcontroller, a digital-signal processor, programmable processor, a computer, a system on a chip, or various combinations thereof. The computing device may include special purpose logic circuitry, for example, a field programmable gate array or an application-specific integrated circuit.

Program instructions (for example, a program, software, software application, script, or code) may be written in various programming languages, including compiled or interpreted languages, declarative or procedural languages, and may be deployed in various forms, for example as a stand-alone program or as a module, component, subroutine, object, or other unit suitable for use in a computing environment. Program instructions may correspond to a file in a file system. Program instructions may be stored in a portion of a file that holds other programs or data (for example, one or more scripts stored in a markup language document), in a dedicated file or in multiple coordinated files (for example, files that store one or more modules, sub-programs, or portions of code). Program instructions may be deployed to be executed on one or more computing devices. A computing device may be located at one site or distributed across multiple sites connected by a network. In other words, a computing device need not be one discreet component, but may be a networked group of components.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed, but that they will include all techniques falling within the scope of the appended claims.

The invention claimed is:

1. A method implemented with a computing device for visualizing historical pathogen sampling in a facility, the method comprising:
   populating, with the computing device, a plurality of sampling locations as a plurality of icons on a map of the facility;
   automatically receiving, at the computing device from a remote database, sampling data specifying a plurality of pathogen levels at the plurality of sampling locations;
   automatically assigning, with the computing device, one of a plurality of colors to each of the plurality of icons according to the plurality of pathogen levels;
   automatically causing coloring, as displayed on a display connected to the computing device, of the plurality of icons on the map with the assigned colors to form a frame;
   automatically repeating, with the computing device, the receiving, assigning, and coloring steps on at least three different occasions to form a sequence of frames;
   automatically causing sequentially displaying, as displayed on the display connected to the computing device, the sequence of frames and an identification of the respective occasion at a constant rate;
   filtering the plurality of icons according to at least one filtering criterion to form a subset of the plurality of icons; and
   not displaying icons excluded from the subset of the plurality of icons during said sequentially displaying the frames,
   wherein:
   the steps that are performed automatically are performed without human intervention;
   the map of the facility is identical n each of the frames in the sequence of frames; and
   the map of the facility is displayed at the same zoom level in each of the frames in the sequence of frames.

2. The method of claim 1, wherein the sequence of frames is filtered according to a time range, such that only frames corresponding to within a period of the time range are sequentially displayed.

3. The method of claim 1, wherein said populating is performed by dragging-and-dropping the plurality of icons, individually.

4. The method of claim 1, further comprising zooming into or out from the map prior to said sequentially displaying the frames, whereby the display of frames is performed at a corresponding zoom level.

5. The method of claim 1, wherein said sequentially displaying the frames is repeated automatically to form a loop.

6. The method of claim 1, further comprising fast-forwarding or rewinding during said sequentially displaying the frames.

7. The method of claim 1, further comprising associating at least one document with an icon.

8. The method of claim 7, further comprising displaying the at least one document by hovering over the given icon.

9. The method of claim 1, wherein the color red is assigned to a given icon when the respective pathogen level exceeds a pre-determined threshold.

10. At least one computer-readable memory storing instructions that, when executed by at least one processor in a computing device, cause operations comprising:
   populating, with the computing device, a plurality of sampling locations as a plurality of icons on a map of the facility;
   automatically receiving, at the computing device from a remote database, sampling data specifying a plurality of pathogen levels at the plurality of sampling locations;
   automatically assigning; with the computing device, one of a plurality of colors to each of the plurality of icons according to the plurality of pathogen levels;
   automatically causing coloring, as displayed on a display connected to the computing device, the pathogen sampling locations on the map with the assigned colors to form a frame;
   automatically repeating, with the computing device, the receiving, assigning, and coloring steps on at least three different occasions to form a sequence of frames;
   automatically causing sequentially displaying, as displayed on the display connected to the computing device, of the sequence of frames and an identification of the respective occasion at a constant rate;
   filtering the plurality of icons according to at least one filtering criterion to form a subset of the plurality of icons; and
   not displaying icons excluded from the subset of the plurality of icons during said sequentially displaying the frames,
   wherein:
   the steps that are performed automatically are performed without human intervention;
   the map of the facility is identical in each of the frames in the sequence of frames; and the map of the facility is displayed at the same zoom level in each of the frames in the sequence of frames.

11. The at least one computer-readable memory of claim 10, wherein the sequence of frames is filtered according to a time range, such that only frames corresponding to within a period of the time range are sequentially displayed.

12. The at least one computer-readable memory of claim 10, wherein said populating is performed by dragging-and-dropping the plurality of icons, individually.

13. The at least one computer-readable memory of claim 10, wherein the operations further comprise zooming into or out from the map prior to said sequentially displaying the frames, whereby the display of frames is performed at a corresponding zoom level.

14. The at least one computer-readable memory of claim 10, wherein said sequentially displaying the frames is repeated automatically to form a loop.

15. The at least one computer-readable memory of claim 10, wherein the operations further comprise fast-forwarding or rewinding during said sequentially displaying the frames.

16. The at least one computer-readable memory of claim 10, wherein the operations further comprise associating at least one document with an icon.

17. The at least one computer-readable memory of claim 16, wherein the operations further comprise displaying the at least one document by hovering over the given icon.

18. The at least one computer-readable memory of claim 10, wherein the color red is assigned to a given icon when the respective pathogen level exceeds a pre-determined threshold.

* * * * *